United States Patent
Aida et al.

(10) Patent No.: US 9,045,411 B2
(45) Date of Patent: Jun. 2, 2015

(54) METHOD FOR RECOVERING ANIONIC FLUORINATED EMULSIFIER

(71) Applicant: ASAHI GLASS COMPANY, LIMITED, Chiyoda-ku (JP)

(72) Inventors: Shigeru Aida, Tokyo (JP); Mizuna Toyoda, Tokyo (JP); Kazuo Hamazaki, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/201,085

(22) Filed: Mar. 7, 2014

(65) Prior Publication Data

US 2014/0187816 A1    Jul. 3, 2014

Related U.S. Application Data

(63) Continuation of application No. PCT/JP2012/072802, filed on Sep. 6, 2012.

(30) Foreign Application Priority Data

Sep. 13, 2011    (JP) .................................. 2011-199724

(51) Int. Cl.
*C07C 229/00*    (2006.01)
*C07C 51/48*    (2006.01)
*B01J 41/04*    (2006.01)
*B01J 49/00*    (2006.01)

(52) U.S. Cl.
CPC ............... *C07C 51/48* (2013.01); *B01J 41/043* (2013.01); *B01J 49/0073* (2013.01)

(58) Field of Classification Search
CPC .............................. C07C 229/12; B01D 61/40
USPC ........... 562/580, 586, 602; 210/643, 665, 666
See application file for complete search history.

(56) References Cited

U.S. PATENT DOCUMENTS

| 4,282,162 A | 8/1981 | Kuhls |
| 6,613,941 B1 | 9/2003 | Felix et al. |
| 8,492,585 B2 * | 7/2013 | Haga et al. ..................... 562/586 |
| 2004/0010156 A1 | 1/2004 | Kondo et al. |
| 2005/0150833 A1 | 7/2005 | Funaki et al. |

FOREIGN PATENT DOCUMENTS

| CN | 1303363 A | 7/2001 |
| CN | 1662451 A | 8/2005 |
| JP | 55-104651 | 8/1980 |
| JP | 63-2656 | 1/1988 |
| JP | 2002-59160 | 2/2002 |
| JP | 2003-285076 | 10/2003 |
| WO | 2011/096448 | 8/2011 |
| WO | WO 2011/096448 | 8/2011 |

OTHER PUBLICATIONS

International Search Report issued Nov. 20, 2012 in PCT/JP2012/072802 filed Sep. 6, 2012.

* cited by examiner

*Primary Examiner* — Sudhakar Katakam
(74) *Attorney, Agent, or Firm* — Oblon, McClelland, Maier & Neustadt, L.L.P.

(57) ABSTRACT

To provide a method for recovering an anionic fluorinated emulsifier, whereby an anionic fluorinated emulsifier adsorbed on a basic ion exchange resin can be simply and efficiently recovered. A mixed liquid of an aqueous inorganic acid solution, a fluorinated medium and a non-fluorinated medium, is contacted to a basic ion exchange resin having an anionic fluorinated emulsifier adsorbed thereon, to recover a liquid phase containing the fluorinated medium, or an aqueous inorganic acid solution is contacted to a basic ion exchange resin having an anionic fluorinated emulsifier adsorbed thereon, then a mixed liquid of a fluorinated medium and a non-fluorinated medium is contacted thereto, and thereafter the basic ion exchange resin and a liquid phase are separated to recover the liquid phase, whereupon from each liquid phase, an acid of the anionic fluorinated emulsifier is recovered.

25 Claims, No Drawings

US 9,045,411 B2

METHOD FOR RECOVERING ANIONIC FLUORINATED EMULSIFIER

TECHNICAL FIELD

The present invention relates to a method for recovering an anionic fluorinated emulsifier, which comprises eluting an anionic fluorinated emulsifier from a basic ion exchange resin having the anionic fluorinated emulsifier adsorbed thereon and recovering it as an acid of the anionic fluorinated emulsifier.

BACKGROUND ART

At the time of producing a fluorinated polymer such as a polytetrafluoroethylene (hereinafter referred to as PTFE), a melt-processable fluororesin or a fluoroelastomer by emulsion polymerization, it is common to use an anionic fluorinated emulsifier in order not to hinder the polymerization reaction by chain transfer in an aqueous medium.

An aqueous emulsion of a fluorinated polymer (hereinafter referred to as a fluorinated polymer aqueous emulsion) obtained by emulsion polymerization is subjected to flocculation, followed by drying, to obtain a powder of the fluorinated polymer. A powder of a fluorinated polymer, particularly a fine powder of PTFE, is molded by a method such as paste extrusion molding and then, used for various applications. Otherwise, if necessary, a nonionic surfactant, etc. may be added to a fluorinated polymer aqueous emulsion for stabilization treatment, followed by concentration treatment to obtain a fluorinated polymer aqueous dispersion containing the fluorinated polymer at a high concentration. Such a fluorinated polymer aqueous dispersion may be used, if necessary, by an addition of various compounding ingredients, for various coating applications, impregnation applications, etc.

On the other hand, an anionic fluorinated emulsifier to be used for emulsion polymerization of a fluorinated polymer is not easily decomposed in the natural world. Therefore, in recent years, it is desired to reduce an anionic fluorinated emulsifier contained not only in industrial effluents but also in products such as a fluorinated polymer aqueous emulsion, a fluorinated polymer aqueous dispersion, etc.

As a method for reducing an anionic fluorinated emulsifier, there is a method wherein a liquid to be treated, such as an aqueous emulsion or an aqueous dispersion, containing an anionic fluorinated emulsifier, is contacted to a basic ion exchange resin, so that the anionic fluorinated emulsifier in the liquid to be treated is adsorbed on the basic ion exchange resin. Further, since the anionic fluorinated emulsifier is expensive, it has been attempted to recover and reuse the anionic fluorinated emulsifier adsorbed on the basic ion exchange resin.

For example, Patent Document 1 discloses a method of treating a basic ion exchange resin having an anionic fluorinated emulsifier adsorbed thereon, with a mixture of a dilute mineral acid and an organic solvent, to recover the emulsifier as an acid of the anionic fluorinated emulsifier. It is disclosed that the organic solvent is preferably a solvent which is miscible with water to present a solubility of at least 40% or which can be unlimitedly mixed with water, and an alcohol such as methanol, a cyclic ether such as dioxane, methylene chloride, etc. may be used.

Further, Patent Document 2 discloses a method wherein by means of an inorganic acid and a water-insoluble fluorinated medium, from a basic ion exchange resin having an anionic fluorinated emulsifier adsorbed thereon, an acid of the anionic fluorinated emulsifier is eluted in the water-insoluble fluorinated medium for recovery.

PRIOR ART DOCUMENTS

Patent Documents

Patent Document 1: JP-B-63-2656
Patent Document 2: WO/2011/096448

DISCLOSURE OF INVENTION

Technical Problem

In Examples of Patent Document 1, an anionic fluorinated emulsifier is recovered in a good yield of at least 80% from a weakly basic ion exchange resin, by using, as an organic solvent, an alcohol such as methanol or a cyclic ether such as dioxane.

However, in the case of eluting and recovering the emulsifier from a strongly basic ion exchange resin having a high ability to adsorb the anionic fluorinated emulsifier, the recovery rate for the anionic fluorinated emulsifier was low at a level of 70%. Further, these organic solvents are flammable and thus require a safety measure for handling. Further, depending upon the type of the anionic fluorinated emulsifier, the emulsifier was likely to react with the alcohol to form an ester, and it was difficult to convert it to an ammonium salt or the like useful as an emulsifier.

Further, in Patent Document 1, an anionic fluorinated emulsifier was recovered by using methylene chloride as a non-flammable organic solvent, but the recovery rate was as low as 50%.

Further, in Patent Document 2, an anionic fluorinated emulsifier was recovered from a basic ion exchange resin having the anionic fluorinated emulsifier adsorbed thereon by using a water-insoluble fluorinated medium as a non-flammable organic solvent, but the recovery rate of the anionic fluorinated emulsifier recovered by a single extraction operation was as low as 50%.

Accordingly, it is an object of the present invention to provide a method for recovering an anionic fluorinated emulsifier, whereby the anionic fluorinated emulsifier adsorbed on a basic ion exchange resin can be simply and efficiently recovered.

Solution to Problem

The present invention provides a method for recovering an anionic fluorinated emulsifier, having the following constructions [1] to [12].

[1] A method for recovering an anionic fluorinated emulsifier, which comprises eluting an anionic fluorinated emulsifier from a basic ion exchange resin having the anionic fluorinated emulsifier adsorbed thereon and recovering it as an acid of the anionic fluorinated emulsifier, and which is characterized by contacting a mixed liquid of an aqueous inorganic acid solution, a fluorinated medium and a non-fluorinated medium, to the basic ion exchange resin, thereafter separating the basic ion exchange resin and a liquid phase to recover the liquid phase, and recovering, from the liquid phase, the acid of the anionic fluorinated emulsifier.

[2] A method for recovering an anionic fluorinated emulsifier, which comprises eluting an anionic fluorinated emulsifier from a basic ion exchange resin having the anionic fluorinated emulsifier adsorbed thereon and recovering it as an acid of the anionic fluorinated emulsifier, and which is characterized by contacting an aqueous inorganic acid solution to the basic ion exchange resin, then contacting a mixed liquid of a fluorinated medium and a non-fluorinated medium thereto, thereafter separating the basic ion exchange resin and a liquid phase to recover the liquid phase, and recovering, from the liquid phase, the acid of the anionic fluorinated emulsifier.

[3] The method for recovering an anionic fluorinated emulsifier according to the above [2], wherein after contacting the aqueous inorganic acid solution to the basic ion exchange resin, the basic ion exchange resin is separated and recovered, and to the separated and recovered basic ion exchange resin, the mixed liquid of a fluorinated medium and a non-fluorinated medium, is contacted.

[4] The method for recovering an anionic fluorinated emulsifier according to any one of the above [1] to [3], wherein the basic ion exchange resin has an average particle size of from 0.1 to 5 mm and an ion exchange capacity of from 0.1 to 3 (eq/L).

[5] The method for recovering an anionic fluorinated emulsifier according to any one of the above [1] to [4], wherein the ratio of the fluorinated medium to the non-fluorinated medium in the mixed liquid is from 5/95 to 95/5 by mass ratio.

[6] The method for recovering an anionic fluorinated emulsifier according to the above [1], [4] or [5], wherein the ratio of the basic ion exchange resin to the mixed liquid of an aqueous inorganic acid solution, a fluorinated medium and a non-fluorinated medium, is from 1/99 to 99/1 by mass ratio.

[7] The method for recovering an anionic fluorinated emulsifier according to any one of the above [2] to [5], wherein the ratio of the basic ion exchange resin to the mixed liquid of a fluorinated medium and a non-fluorinated medium, is from 1/99 to 80/20 by mass ratio.

[8] The method for recovering an anionic fluorinated emulsifier according to any one of the above [1] to [7], wherein the aqueous inorganic acid solution is at least one member selected from the group consisting of aqueous solutions of hydrochloric acid, sulfuric acid, nitric acid and phosphoric acid.

[9] The method for recovering an anionic fluorinated emulsifier according to any one of the above [1] to [8], wherein the fluorinated medium is at least one member selected from the group consisting of 1,3-dichloro-1,1,2,2,3-pentafluoropropane, 1,1-dichloro-2,2,3,3,3-pentafluoropropane, $CF_3CF_2CF_2CF_2CF_2CHF_2$ and $CF_3CH_2OCF_2CF_2H$.

[10] The method for recovering an anionic fluorinated emulsifier according to any one of the above [1] to [9], wherein the non-fluorinated medium is water-soluble and has a solubility in the fluorinated medium.

[11] The method for recovering an anionic fluorinated emulsifier according to any one of the above [1] to [10], wherein the non-fluorinated medium is at least one member selected from the group consisting of acetone, acetonitrile, tetrahydrofuran, diethyl ether, methyl acetate, ethyl acetate, methanol, ethanol, n-propanol, iso-propanol and tert-butanol.

[12] The method for recovering an anionic fluorinated emulsifier according to the above [1], wherein the mixed liquid of an aqueous inorganic acid solution, a fluorinated medium and a non-fluorinated medium, is non-flammable.

[13] The method for recovering an anionic fluorinated emulsifier according to the above [2] or [3], wherein the mixed liquid of a fluorinated medium and a non-fluorinated medium, is non-flammable.

[14] The method for recovering an anionic fluorinated emulsifier according to any one of the above [1] to [13], wherein the acid of the anionic fluorinated emulsifier is a fluorinated carboxylic acid.

[15] The method for recovering an anionic fluorinated emulsifier according to the above [14], wherein the acid of the anionic fluorinated emulsifier is a $C_{5-7}$ fluorinated carboxylic acid which may have from 1 to 3 etheric oxygen atoms.

[16] The method for recovering an anionic fluorinated emulsifier according to any one of the above [1] to [15], wherein the basic ion exchange resin is a strongly basic ion exchange resin.

Advantageous Effects of Invention

According to the present invention, to a basic ion exchange resin having an anionic fluorinated emulsifier adsorbed thereon, a mixed liquid of an aqueous inorganic acid solution, a fluorinated medium and a non-fluorinated medium is contacted, or to such a basic ion exchange resin, an aqueous inorganic acid solution is contacted, and then, a mixed liquid of a fluorinated medium and a non-fluorinated medium is contacted thereto, whereby the anionic fluorinated emulsifier adsorbed on the basic ion exchange resin is converted to an acid-form by the aqueous inorganic acid solution and eluted in the fluorinated medium and the non-fluorinated medium. And, in the present invention, a fluorinated medium and a non-fluorinated medium are used in combination for extraction, whereby the extraction can be made more efficiently than a case where the fluorinated medium and the non-fluorinated medium are used alone independently, and an acid of the anionic fluorinated emulsifier can be recovered in good yield. The recovered acid of the anionic fluorinated emulsifier may be used, as it is, for emulsion polymerization for a fluorinated polymer, or may be neutralized and used as e.g. an ammonium salt or an alkali metal salt.

DESCRIPTION OF EMBODIMENTS

In the present invention, the anionic fluorinated emulsifier to be adsorbed on a basic ion exchange resin is not particularly limited. For example, it may be a fluorinated carboxylic acid which may have an etheric oxygen atom or its salt, or a fluorinated sulfonic acid or its salt. The salt may, for example, be an ammonium salt or an alkali metal salt (such as Li, Na or K), preferably an ammonium salt. Among them, a fluorinated carboxylic acid which may have an etheric oxygen atom, or its salt, is preferred, and a $C_{5-7}$ fluorinated carboxylic acid which may have from 1 to 3 etheric oxygen atoms, or its salt, is more preferred.

Specific examples of the fluorinated carboxylic acid include, a perfluorocarboxylic acid, a perfluorocarboxylic acid having an etheric oxygen atom, a fluorinated carboxylic acid having a hydrogen atom, etc.

The perfluorocarboxylic acid includes, for example, perfluorohexanoic acid, perfluoroheptanoic acid, perfluorooctanoic acid, perfluorononanoic acid, etc The perfluorocarboxylic acid having an etheric oxygen atom includes, for example, $C_3F_7OCF(CF_3)CF_2OCF(CF_3)$ COOH, $C_4F_9OC_2F_4OCF_2COOH$, $C_3F_7OC_2F_4OCF_2COOH$, $C_2F_5OC_2F_4OCF_2COOH$, $C_2F_5OCF_2CF_2OCF_2CF_2OCF_2COOH$, $C_2F_5O(CF_2)_5COOH$, $CF_3OC_2F_4OCF_2COOH$, $CF_3OCF_2OCF_2OCF_2COOH$, $CF_3OCF_2OCF_2OCF_2OCF_2COOH$, $CF_3O(CF_2CF_2O)_2CF_2COOH$, $CF_3OCF_2CF_2CF_2OCF_2COOH$, $C_4F_9OCF_2COOH$, $C_4F_9OCF_2CF_2COOH$, $CF_3OCF(CF_3)CF_2OCF(CF_3)COOH$, $C_4F_9OCF(CF_3)COOH$, etc.

The fluorinated carboxylic acid having a hydrogen atom includes, for example, ω-hydroperfluorooctanoic acid, $C_3F_7OCF(CF_3)CF_2OCHFCOOH$, $CF_3CFHO(CF_2)_5COOH$, $CF_3O(CF_2)_3OCHFCF_2COOH$, $CF_3O(CF_2)_3OCHFCOOH$, $C_3F_7OCHFCF_2COOH$, $CF_3CFHO(CF_2)_3COOH$, etc.

The fluorinated sulfonic acid includes, for example, perfluorooctane sulfonic acid, $C_6F_{13}CH_2CH_2SO_3H$, etc.

In the present invention, the basic ion exchange resin to be used for adsorbing the anionic fluorinated emulsifier may be a strongly basic ion exchange resin or a weakly basic ion exchange resin, preferably a strongly basic ion exchange resin. The strongly basic ion exchange resin is less susceptible to an influence by the pH of the liquid to be treated containing the anionic fluorinated emulsifier and thus can maintain high adsorbing efficiency. Further, the strongly basic ion exchange resin adsorbs the anionic fluorinated emulsifier firmly so that the anionic fluorinated emulsifier tends to be hardly eluted from the strongly basic ion exchange resin, whereby the recovery rate of the anionic fluorinated emulsifier tends to be low, but by the method of the present invention, even in a case where the anionic fluorinated emulsifier is adsorbed on the strongly basic ion exchange resin, the anionic fluorinated emulsifier can be recovered in good yield.

The strongly basic ion exchange resin may be one having a quaternary ammonium group such as a trimethylammonium group or a dimethylethanolammonium group introduced as an ion exchange group to a resin matrix.

The weakly basic ion exchange resin may be one having a primary to tertiary amino group such as a dimethylammonium group or an amino group introduced as an ion exchange group to a resin matrix.

The material for the resin matrix of the basic ion exchange resin is not particularly limited. A styrene/divinyl benzene cross-linked resin, an acryl/divinyl benzene cross-linked resin or a cellulose resin may, for example, be mentioned.

The type of the basic ion exchange resin is not particularly limited, and either porous type or gel type may be preferably used.

The average particle size of the basic ion exchange resin is preferably from 0.1 to 5 mm, more preferably from 0.2 to 2 mm, particularly preferably from 0.3 to 1.5 mm. When the average particle size of the basic ion exchange resin is within the above range, for example, the flow path of the liquid to be treated is less likely to be clogged, when the liquid to be treated containing the anionic fluorinated emulsifier is permitted to flow through a column packed with the basic ion exchange resin to carry out the operation to let the anionic fluorinated emulsifier be adsorbed.

The ion exchange capacity of the basic ion exchange resin is preferably from 0.1 to 3 (eq/L), more preferably from 0.5 to 2.5 (eq/L). When the ion exchange capacity of the basic ion exchange resin is within the above range, the anionic fluorinated emulsifier in the liquid to be treated can efficiently be adsorbed.

Commercial products of the basic ion exchange resin include, for example, Lewatit (registered trademark) MP8000H manufactured by Lanxess, Lewatit (registered trademark) M800KR manufactured by Lanxess, Lewatit (registered trademark) MP600 manufactured by Lanxess, Lewatit (registered trademark) MP62WS manufactured by Lanxess, PUROLITE (registered trademark) A300 MBOH manufactured by Purolite K.K., PUROLITE (registered trademark) A503OH manufactured by Purolite K.K., etc.

In the present invention, the basic ion exchange resin having an anionic fluorinated emulsifier adsorbed thereon, is obtainable by contacting a liquid to be treated containing an anionic fluorinated emulsifier to a basic ion exchange resin. That is, by contacting the liquid to be treated, to a basic ion exchange resin, the anionic fluorinated emulsifier in the liquid to be treated, is adsorbed on the basic ion exchange resin. For example, in a case where a liquid to be treated containing $CF_3CF_2OCF_2CF_2OCF_2COO^-$ $(NH4)^+$ as an anionic fluorinated emulsifier is contacted with a basic ion exchange resin, $CF_3CF_2OCF_2CF_2OCF_2COO^-$ is considered to be bonded to and adsorbed on an ion exchange group of the basic ion exchange resin.

As the liquid to be treated containing an anionic fluorinated emulsifier, the following (1) to (3) may, for example, be mentioned.

(1) A fluorinated polymer aqueous dispersion obtained by subjecting a fluorinated monomer to emulsion polymerization in the presence of an anionic fluorinated emulsifier, and adding a nonionic surfactant to the obtained fluorinated polymer aqueous emulsion for stabilization, if required, followed by concentration.

(2) Waste water containing an anionic fluorinated emulsifier discharged after flocculating the above fluorinated polymer aqueous emulsion.

(3) An aqueous solution having absorbed an anionic fluorinated emulsifier discharged in the atmosphere in the process for drying a fluorinated polymer flocculate obtained by flocculating the above fluorinated polymer aqueous emulsion.

The above fluorinated polymer dispersion is preferably a fluorinated polymer aqueous dispersion obtained by stabilizing the fluorinated polymer aqueous emulsion by a nonionic surfactant.

The nonionic surfactant may, for example, be a surfactant represented by the following formula (A) or (B).

$$R^1\text{—O-A-H} \tag{A}$$

In the formula (A), $R^1$ is a $C_{8-18}$ alkyl group, and A is a polyoxyalkylene group constituted by from 5 to 20 oxyethylene groups and from 0 to 2 oxypropylene groups.

$$R^2\text{—}C_6H_4\text{—O—B-H} \tag{B}$$

In the formula (B), $R^2$ is a $C_{4-12}$ alkyl group, and B is a polyoxyethylene group constituted by from 5 to 20 oxyethylene groups.

Specific examples of the nonionic surfactant of the formula (A) include nonionic surfactants having molecular structures of $C_{13}H_{27}(OC_2H_4)_{10}$—OH, $C_{12}H_{25}(OC_2H_4)_{10}$—OH, $C_{10}H_{21}CH(CH_3)CH_2$—$(OC_2R_4)_9$—OH, $C_{13}H_{27}$—$(OC_2H_4)_8$—$OCH(CH_3)CH_2$—OH, $C_{16}H_{33}$—$(OC_2H_4)_{10}$—OH, $CH(C_5H_{11})(C_7H_{15})$—$(OC_2H_4)_9$—OH, etc. Commercial products include TERGITOL (registered trademark) 15S series, manufactured by The Dow Chemical Company, Newcol (registered trademark) series, manufactured by Nippon Nyukazai Co., Ltd., Lionol (registered trademark) TD series, manufactured by Lion Corporation, etc.

Specific examples of the nonionic surfactant of the formula (B) include, for example, nonionic surfactants having molecular structures of $C_8H_{17}$—$C_6H_4$—$(OC_2H_4)_{10}$—OH, $C_9H_{19}$—$C_6H_4$—$(OC_2H_4)_{10}$—OH, etc. Commercial products include Triton (registered trademark) X series, manufactured by The Dow Chemical Company, Nikkol (registered trademark) OP series or NP series, manufactured by Nikko Chemicals Co., Ltd., etc.

The content of a nonionic surfactant represented by the formula (A) and/or (B) in the fluorinated polymer aqueous dispersion is preferably from 1 to 20 mass %, more preferably from 1 to 10 mass %, particularly preferably from 2 to 8 mass %, based on the mass of the fluorinated polymer.

The method for contacting the liquid to be treated containing an anionic fluorinated emulsifier and the basic ion exchange resin is not particularly limited, and a conventional method may be mentioned. For example, it may be a method of putting the basic ion exchange resin into the liquid to be treated, followed by stirring or vibrating, or a method of passing the liquid to be treated, through a column packed with the basic ion exchange resin. Further, prior to contacting the liquid to be treated, to the basic ion exchange resin, the liquid to be treated may preferably be subjected to filtration to remove any floating solid, etc. such as coagulation, whereby it is possible to prevent e.g. clogging of the basic ion exchange resin. Such filtration of the liquid to be treated, is preferably conducted by means of a single stage or multistage filters having openings of from 0.1 to 300 μm, preferably from 1 to 100 μm.

The contact temperature at the time of contacting the liquid to be treated containing an anionic fluorinated emulsifier to the basic ion exchange resin is not particularly limited. It may suitably be selected but is preferably in the vicinity of room temperature of from 10 to 40° C. Further, the contact time is not particularly limited and may suitably be selected. For example, in the case of contacting by a stirring system, it is preferably within a range of from 10 minutes to 200 hours, more preferably within a range of from 30 minutes to 50 hours. Further, the pressure at the time of contact is preferably the atmospheric pressure, but it may be under a reduced pressure condition or an elevated pressure condition.

As mentioned above, by letting an anionic fluorinated emulsifier in the liquid to be treated, be adsorbed on a basic ion exchange resin, followed by separating the basic ion exchange resin, it is possible to obtain the basic ion exchange resin having the anionic fluorinated emulsifier adsorbed thereon. Such a basic ion exchange resin having the anionic fluorinated emulsifier adsorbed thereon may be used in a wet state without conducting drying treatment, etc. or may be subjected to drying treatment and used in a dried state. Industrially, it is preferred to use it as it is in a wet state, whereby the process can be simplified.

In a first embodiment of the method for recovering an anionic fluorinated emulsifier in the present invention, firstly a mixed liquid of an aqueous inorganic acid solution, a fluorinated medium and a non-fluorinated medium (hereinafter the mixed liquid of an aqueous inorganic acid solution, a fluorinated medium and a non-fluorinated medium will be referred to as the elution extraction medium), is contacted to the basic ion exchange resin having an anionic fluorinated emulsifier adsorbed thereon.

When the elution extraction medium is contacted to the basic ion exchange resin having an anionic fluorinated emulsifier adsorbed thereon, the anionic fluorinated emulsifier is converted to an acid-form by the aqueous inorganic acid solution and thus tends to be easily eluted from the basic ion exchange resin. The anionic fluorinated emulsifier has good compatibility with the fluorinated medium and the non-fluorinated medium, and therefore, the anionic fluorinated emulsifier adsorbed on the basic ion exchange resin is eluted as an acid of the anionic fluorinated emulsifier and extracted in the fluorinated medium and the non-fluorinated medium. And, in the present invention, by the combined use of the fluorinated medium and the non-fluorinated medium, it is possible to more efficiently extract the acid of the anionic fluorinated emulsifier than a case where the fluorinated medium and the non-fluorinated medium are used alone independently. Thus, it is possible to recover the acid of the anionic fluorinated emulsifier in good yield from the basic ion exchange resin.

Here, if only the aqueous inorganic acid solution is contacted to the basic ion exchange resin, the acid of the anionic fluorinated emulsifier is not substantially extracted in the aqueous inorganic acid solution, and it is considered to be attached to the surface of the basic ion exchange resin. Therefore, as disclosed in Comparative Example 1 in WO/2011/096448, even if an aqueous inorganic acid solution is contacted to a basic ion exchange resin having an anionic fluorinated emulsifier adsorbed thereon, followed by addition of a fluorinated solvent in an attempt to extract the anionic fluorinated emulsifier, the acid of the anionic fluorinated emulsifier cannot substantially be extracted.

The ratio of the basic ion exchange resin to the elution extraction medium is preferably basic ion exchange resin/elution extraction medium=from 1/99 to 99/1, more preferably from 10/90 to 90/10, most preferably from 15/85 to 50/50, by mass ratio. When the ratio of the basic ion exchange resin to the elution extraction medium is within the above range, it is possible to efficiently contact the basic ion exchange resin and the elution extraction medium.

The contact time of the basic ion exchange resin and the elution extraction medium is preferably from 5 to 500 minutes, more preferably from 10 to 300 minutes. When the contact time is at least 5 minutes, it is possible to sufficiently extract the acid of the anionic fluorinated emulsifier. Even if the contact time exceeds 500 minutes, there is no substantial change in the amount of extraction of the acid of the anionic fluorinated emulsifier, and therefore, the upper limit is preferably 500 minutes.

The temperature at the time of contacting the elution extraction medium is preferably from 5 to 100° C., more preferably from 10 to 80° C. When it is at least 5° C., it is possible to efficiently extract the acid of the anionic fluorinated emulsifier. When it is at most 100° C., it does not exceed the boiling point under the atmospheric pressure of a preferred solvent, whereby the extraction operation can be conducted under the atmospheric pressure, and therefore, the upper limit is preferably 100° C.

The method for contacting the basic ion exchange resin and the elution extraction medium is not particularly limited. For example, a method of putting the basic ion exchange resin and the elution extraction medium in an autoclave, followed by mechanical stirring by stirring vanes, or a method of contacting the basic ion exchange resin and the elution extraction medium by means of a shaking machine, may be mentioned. Otherwise, the basic ion exchange resin may be packed in a column, and the elution extraction medium is permitted to flow therethrough, so that the acid of the anionic fluorinated emulsifier may be extracted in the elution extraction medium by a flow-through extraction method. Here, in the case of extracting the anionic fluorinated emulsifier in the elution extraction medium by the flow-through extraction method from the basic ion exchange resin packed in a column, it is preferred that the mixing ratio of the aqueous inorganic acid solution, the fluorinated medium and the non-fluorinated medium is adjusted to a composition wherein the elution extraction medium becomes a single phase. The composition wherein the elution extraction medium becomes a single phase, varies depending upon the types of the aqueous inorganic acid solution, the fluorinated medium and the non-fluorinated medium, but by adjusting the ratio of the water-soluble non-fluorinated medium to be a ratio sufficient to be dissolved in the aqueous inorganic acid solution, the composition may be made wherein the elution extraction medium becomes a single phase.

As the aqueous inorganic acid solution, at least one member selected from the group consisting of aqueous solutions of hydrochloric acid, sulfuric acid and phosphoric acid, is preferably used. Two or more types of such aqueous inorganic acid solutions may be used in combination. Among them, an aqueous hydrochloric acid solution is particularly preferred, since its use is industrially simple.

The concentration of the aqueous inorganic acid solution is usually preferably high, since as it becomes high, the acid of the anionic fluorinated emulsifier to be eluted from the basic ion exchange resin tends to increase. It is preferably at least 1.0 mass %, more preferably at least 5.0 mass %, particularly preferably from 10 to 38 mass %.

As the fluorinated medium, at least one member selected from the group consisting of a hydrochlorofluorocarbon, a hydrofluorocarbon, a hydrofluoroether and a hydrofluoroalcohol is preferably used. Among them, a hydrochlorofluorocarbon, a hydrofluorocarbon or a hydrofluoroether is preferred.

The hydrochlorofluorocarbon includes 1,3-dichloro-1,1,2,2,3-pentafluoropropane, 1,1-dichloro-2,2,3,3,3-pentafluorocarbon, etc.

The hydrofluorocarbon includes $CF_3CF_2CF_2CF_2CF_2CHF_2$, $CF_3CF_2CF_2CF_2CH_2CH_3$, $CF_3CF_2CF_2CF_2CF_2CF_2CH_2CH_3$, $CF_3CF_2CHFCHFCF_3$, $CF_3CH_2CF_2CH_3$, $CF_3CF_2CF_2CFHCFH_3$, etc.

The hydrofluoroether includes $CF_3CH_2OCF_2CF_2H$, $CF_3CH_2OCF_2CFHCF_3$, $(CF_3)_2CHOCF_2CF_2H$, $CF_3CH_2OCHFCHF_2$, $CF_3(CF_2)_3OCH_3$, $CF_3(CF_2)_4OCH_3$, $CF_3(CF_2)_3OCH_2CH_3$, $CF_3(CF_2)_4OCH_2CH_3$, $(CF_3)_2CFCF_2OCH_2CH_3$, etc.

The hydrofluoroalcohol includes 2,2,2-trifluoroethanol, 2,2,3,3-tetrafluoropropanol, 1,1,1,3,3,3-hexafluoroisopropanol, 2,2,3,3,3-pentafluoropropanol, etc.

Here, in a case where the anionic fluorinated emulsifier to be extracted from the basic ion exchange resin does not form an ester by a reaction with a hydrofluoroalcohol or in a case where there is no problem even if such an ester is formed, it is possible to use the hydrofluoroalcohol.

The fluorinated medium is preferably water-insoluble, and it is most preferred that the solubility in water at 25° C., is less than 0.1%. When it is water-insoluble, the elution extraction medium tends to be readily separated to a phase of the fluorinated medium and a phase of the aqueous inorganic acid solution, whereby it is possible to recover the liquid phase containing a large amount of the acid of the anionic fluorinated emulsifier by a simple operation.

Among them, 1,3-dichloro-1,1,2,2,3-pentafluoropropane, 1,1-dichloro-2,2,3,3,3-pentafluoropropane, $CF_3CF_2CF_2CF_2CF_2CHF_2$ or $CF_3CH_2OCF_2CF_2H$ is particularly preferably used, since the affinity to both the anionic fluorinated emulsifier and the non-fluorinated medium is good.

The non-fluorinated medium is one which has no fluorine atom in its molecule, and one which is water-soluble and has solubility in the fluorinated medium is preferably used. When the non-fluorinated medium is water-soluble and has solubility in the fluorinated medium, the penetrability of the elution extraction medium to the basic ion exchange resin will be good, whereby it becomes easy to extract the anionic fluorinated emulsifier from the basic ion exchange resin.

The solubility in water at 25° C. of the non-fluorinated medium is preferably at least 50%, more preferably at least 90%. Further, the solubility in the fluorinated medium at 25° C. of the non-fluorinated medium is preferably at least 50%, more preferably at least 90%.

Specific examples of the non-fluorinated medium include an alcohol such as methanol, ethanol, n-propanol, iso-propanol or tert-butanol; a ketone such as acetone or methyl ethyl ketone; a nitrile such as acetonitrile; an ether such as tetrahydrofuran, dimethyl ether, diethyl ether or methyl ethyl ether; an ester such as methyl acetate or ethyl acetate; an amide such as N,N-dimethylformamide; a pyrrolidone such as N-methylpyrrolidone; and a sulfoxide such as dimethyl sulfoxide.

Each of the above-mentioned non-fluorinated media is water-soluble and has solubility in a fluorinated medium. Among them, acetone, acetonitrile, tetrahydrofuran, diethyl ether, methyl acetate, ethyl acetate, methanol, ethanol, n-propanol, iso-propanol or tert-butanol is preferred, and acetone or acetonitrile is most preferred. Here, in a case where the acid of the anionic fluorinated emulsifier to be extracted from the basic ion exchange resin is likely to be reacted with an alcohol to form an ester thereby to cause a problem at the time of conversion to e.g. an ammonium salt useful as an emulsifier, use of an alcohol should better be avoided. An alcohol may be used in a case where it does not form an ester with the acid of the anionic fluorinated emulsifier or in a case where there is no problem even when such an ester is formed.

In the elution extraction medium, the ratio of the aqueous inorganic acid solution to the fluorinated medium is preferably aqueous inorganic acid solution/fluorinated medium=from 1/99 to 95/5, more preferably from 5/95 to 80/20, particularly preferably from 10/90 to 70/30, by mass ratio. When the mass ratio of the aqueous inorganic acid solution to the fluorinated medium is within the above range, the recovery rate of the acid of the anionic fluorinated emulsifier is high.

Further, in the elution extraction medium, the ratio of the fluorinated medium to the non-fluorinated medium is preferably fluorinated medium/non-fluorinated medium=from 5/95 to 95/5, more preferably from 10/90 to 95/5, particularly preferably from 15/85 to 95/5, by mass ratio. When the mass ratio of the fluorinated medium to the non-fluorinated medium is within the above range, the recovery rate of the acid of the anionic fluorinated emulsifier is high.

Further, by adjusting the mass ratio of the fluorinated medium to the non-fluorinated medium to be from 75/25 to 95/5, preferably from 85/15 to 95/5, the elution extraction medium tends to be non-flammable, and its handling efficiency will be excellent. For example, in a case where 1,3-dichloro-1,1,2,2,3-pentafluoropropane is used as the fluorinated medium and acetone is used as the non-fluorinated medium, by adjusting the ratio to be fluorinated medium/non-fluorinated medium=from 85/15 to 95/5 by mass ratio, the elution extraction medium will be non-flammable. Further, in a case where 1,3-dichloro-1,1,2,2,3-pentafluoropropane is used as the fluorinated medium and acetonitrile is used as the non-fluorinated medium, by adjusting the ratio to be fluorinated medium/non-fluorinated medium=from 75/25 to 95/5 by mass ratio, the elution extraction medium will be non-flammable.

In the above embodiment, from the mixture of the basic ion exchange resin and the elution extraction medium, the basic ion exchange resin is separated and removed, and a liquid phase is separated and recovered, and from the recovered liquid phase, the acid of the anionic fluorinated emulsifier is recovered. In a case where the recovered liquid phase is a single phase (the aqueous inorganic acid solution, the fluorinated medium and the non-fluorinated medium constitute a mixed phase), by carrying out e.g. a distillation operation of the recovered phase, the acid of the anionic fluorinated emulsifier can be recovered.

Whereas, in a case where as the fluorinated medium, one which is water-insoluble is used, and as the non-fluorinated medium, one which is water-soluble and has solubility in the fluorinated medium, is used, the system will be separated into two layers i.e. an upper layer wherein the non-fluorinated medium is dissolved in the aqueous inorganic acid solution and a lower layer wherein the non-fluorinated medium is dissolved in the fluorinated medium. Also in the upper layer, the acid of the anionic fluorinated emulsifier will be slightly present, and in the lower layer containing the fluorinated medium, the acid of the anionic fluorinated emulsifier is present at a high concentration. Its presence in the upper layer is extremely small as compared with the lower layer. Therefore, by taking only the lower layer by separation, it is possible to efficiently recover the acid of the anionic fluorinated emulsifier.

The acid of the anionic fluorinated emulsifier contained in the recovered liquid (the lower layer in the case where only the lower layer is taken by separation) can be quantitatively analyzed by e.g. an analytical method disclosed in JIS quality of water K0400-30-10, an analytical method by gas chromatography, or an NMR analytical method using $^{1}$H-NMR and $^{19}$F-NMR.

The acid of the anionic fluorinated emulsifier thus recovered may be used as it is as an anionic fluorinated emulsifier, or may be neutralized and used as an ammonium salt, an alkali metal salt or the like.

Now, a second embodiment of the method for recovering an anionic fluorinated emulsifier in the present invention will be described.

In the second embodiment, an aqueous inorganic acid solution is contacted to a basic ion exchange resin having an anionic fluorinated emulsifier adsorbed thereon, and then, a mixed liquid of a fluorinated medium and a non-fluorinated medium (the mixed liquid of a fluorinated medium and a non-fluorinated medium will hereinafter be referred to as the extraction medium) is contacted thereto.

As mentioned above, when an aqueous inorganic acid solution is contacted to the basic ion exchange resin, the anionic fluorinated emulsifier is converted to an acid-form and adsorbed on the basic ion exchange resin in a form to be readily eluted. The anionic fluorinated emulsifier has low compatibility with the aqueous inorganic acid solution, whereby even if converted to an acid-form, it will scarcely be eluted in the aqueous inorganic acid solution. However, the anionic fluorinated emulsifier has good compatibility with the fluorinated medium and the non-fluorinated medium, and when the extraction medium is contacted to the basic ion exchange resin contacted with the aqueous inorganic acid solution, the anionic fluorinated emulsifier adsorbed on the basic ion exchange resin will be eluted and extracted as an acid of the anionic fluorinated emulsifier in the extraction medium. Then, the basic ion exchange resin is separated and removed, and the liquid phase is recovered. In a case where the recovered liquid phase is in the form of a single phase, the acid of the anionic fluorinated emulsifier can be recovered by carrying out e.g. a distillation operation of the recovered liquid phase. Otherwise, in a case where the recovered liquid phase is separated into two layers, the acid of the anionic fluorinated emulsifier is present at a high concentration in a lower layer containing the fluorinated medium, and therefore, by taking only the lower layer by separation, it is possible to efficiently recover the acid of the anionic fluorinated emulsifier.

In the second embodiment, it is preferred that after contacting the aqueous inorganic acid solution to the basic ion exchange resin, the basic ion exchange resin is separated and recovered, and a mixed liquid of the fluorinated medium and the non-fluorinated medium is contacted to the separated and recovered basic ion exchange resin. Thus, an operation to separate the aqueous inorganic acid solution and the extraction liquid becomes unnecessary, and the liquid phase wherein the acid of the anionic fluorinated emulsifier is present at a high concentration can be recovered by an extremely simple operation. Further, in a case where the non-fluorinated medium is decomposed by a reaction with the inorganic acid, it is possible to minimize the amount of the inorganic acid in contact with the non-fluorinated medium so that the decomposition of the non-fluorinated medium can be minimized.

In the second embodiment, as the aqueous inorganic acid solution, the fluorinated medium and the non-fluorinated medium, the same ones as described above in the first embodiment may be used.

In the second embodiment, the contact time of the basic ion exchange resin and the aqueous inorganic acid solution is preferably from 5 to 500 minutes, more preferably from 10 to 300 minutes. When the contact time is at least 5 minutes, the anionic fluorinated emulsifier can be converted to an acid-form and can be made to be readily eluted from the basic ion exchange resin. Further, even if it exceeds 500 minutes, there will be no substantial improvement in effects, and therefore, the upper limit is preferably 500 minutes.

The temperature at the time of contacting the aqueous inorganic acid solution is preferably from 5 to 100° C., more preferably from 10 to 80° C. When it is at least 5° C., the anionic fluorinated emulsifier can be converted to an acid-form and can be made to be readily eluted from the basic ion exchange resin. When it is at most 100° C., it does not exceed the boiling point under the atmospheric pressure of the aqueous inorganic acid solution, so that the treatment by the aqueous inorganic acid solution can be carried out under the atmospheric pressure, and therefore, the upper limit is preferably 100° C.

In the second embodiment, the method for contacting the basic ion exchange resin and the aqueous inorganic acid solution is not particularly limited. For example, a method of putting the basic ion exchange resin and the aqueous inorganic acid solution in an autoclave, followed by mechanical stirring by stirring vanes, or a method of contacting the basic ion exchange resin and the aqueous inorganic acid solution by means of a shaking machine, may be mentioned. Otherwise, the basic ion exchange resin may be packed in a column, and the aqueous inorganic acid solution is permitted to flow therethrough for the contact.

In the second embodiment, the ratio of the basic ion exchange resin to the aqueous inorganic acid solution is preferably from 99/1 to 1/99, more preferably from 90/10 to 10/90, most preferably from 60/40 to 30/70, by mass ratio. When the ratio of the basic ion exchange resin to the aqueous inorganic acid solution is within the above range, it is possible to efficiently contact the basic ion exchange resin and the aqueous inorganic acid solution, and the anionic fluorinated emulsifier adsorbed on the basic ion exchange resin can be made to be readily eluted.

In the second embodiment, the contact time of the basic ion exchange resin and the extraction medium is preferably from 5 to 500 minutes, more preferably from 10 to 300 minutes. When the contact time is at least 5 minutes, it is possible to sufficiently extract the anionic fluorinated emulsifier. Even if the contact time exceeds 500 minutes, there is no substantial change in the amount of extraction of the acid of the anionic fluorinated emulsifier, and therefore, the upper limit is preferably 500 minutes.

The temperature at the time of contacting the extraction medium is preferably from 5 to 100° C., more preferably from 10 to 80° C. When it is at least 5° C., it is possible to efficiently extract the acid of the anionic fluorinated emulsifier. When it is at most 100° C., it does not exceed the boiling point under the atmospheric pressure of a preferred solvent, whereby the extraction operation can be conducted under the atmospheric pressure, and therefore, the upper limit is preferably 100° C.

In the second embodiment, the method for contacting the basic ion exchange resin and the extraction medium may be carried out by the same method as the above-mentioned method for contacting the aqueous inorganic acid solution.

In the second embodiment, in the extraction medium, the ratio of the fluorinated medium to the non-fluorinated medium is preferably fluorinated medium/non-fluorinated medium=from 5/95 to 95/5, more preferably from 10/90 to 90/10, particularly preferably from 20/80 to 90/10, by mass ratio. When the mass ratio of the fluorinated medium to the non-fluorinated medium is within the above range, the recovery rate of the acid of the anionic fluorinated emulsifier is high. Further, by adjusting the mass ratio of the fluorinated medium to the non-fluorinated medium to be from 75/25 to 95/5, preferably from 85/15 to 95/5, the extraction medium tends to be non-flammable, and its handling efficiency will be excellent.

In the second embodiment, the ratio of the basic ion exchange resin to the extraction medium is preferably from 1/99 to 80/20, more preferably from 10/90 to 70/30, most preferably from 15/85 to 60/40, by mass ratio. When the ratio of the basic ion exchange resin to the extraction medium is within the above range, it is possible to efficiently contact the basic ion exchange resin and the extraction medium and extract the acid of the anionic fluorinated emulsifier in the extraction medium.

EXAMPLES

Now, the present invention will be described in further detail with reference to working Examples (Ex 1-1 to 1-12, and 2-1 to 2-20) and comparative Examples (Ex 1-13, 1-14 and 2-21), but it should be understood that the present invention is by no means limited thereto.

[Flammability of Elution Extraction Medium and Extraction Medium]

Presence or absence of flammability of the elution extraction medium or the extraction medium used in each Ex was confirmed by a Tag closed method as disclosed in JIS K2265-1 or by a Cleveland open system as disclosed in JIS K2265-4.

[Recovery Rate of Anionic Fluorinated Emulsifier]

With respect to a liquid phase recovered after extraction treatment, the acid of the anionic fluorinated emulsifier was quantitatively analyzed by quantitative analyses by $^1$H-NMR and $^{19}$F-NMR, and the content (g) of the acid of the anionic fluorinated emulsifier in the liquid phase was measured. Then, the recovery rate of the acid of the anionic fluorinated emulsifier was obtained based on the following formula.

Recovery rate(%)=(content (g) of the acid of the anionic fluorinated emulsifier in the liquid phase/ amount (g) of the anionic fluorinated emulsifier adsorbed on the basic ion exchange resin)×100

Ex 1

An aqueous solution of an anionic fluorinated emulsifier ($CF_3CF_2OCF_2CF_2OCF_2COO^-(NH_4)^+$) and a basic ion exchange resin were contacted to let the anionic fluorinated emulsifier be adsorbed on the basic ion exchange resin.

Then, into a beaker having an internal capacity of 50 ml and provided with a cover, the basic ion exchange resin having the anionic fluorinated emulsifier adsorbed thereon, hydrochloric acid, a non-fluorinated medium and a fluorinated medium were charged as shown in Table 1, and the content was stirred for from 10 to 60 minutes by a magnetic stirrer while maintaining the temperature at 40° C. by a constant temperature water bath, to carry out extraction of an acid of the anionic fluorinated emulsifier.

After completion of the stirring, the basic ion exchange resin was separated and removed. Then, in Ex 1-1 to 1-13, as the liquid phase remaining by separating and removing the basic ion exchange resin was separated into two layers, only the lower layer was recovered. Further, in Ex 1-14, as the liquid phase remaining by separating and removing the basic ion exchange resin constituted a single phase, the liquid phase was recovered as it was.

Thereafter, the acid of the anionic fluorinated emulsifier contained in the recovered liquid phase (the lower layer in the case where only the lower layer was recovered) was quantitatively analyzed by the above-mentioned method, and the recovery rate of the acid of the anionic fluorinated emulsifier was measured. The results are summarized in Table 1.

TABLE 1

| | NO. | Ex 1-1 | Ex 1-2 | Ex 1-3 | Ex 1-4 | Ex 1-5 | Ex 1-6 | Ex 1-7 |
|---|---|---|---|---|---|---|---|---|
| | Type of basic ion exchange resin | IER-1 | IER-1 | IER-1 | IER-1 | IER-1 | IER-1 | IER-1 |
| | Amount (g) of basic ion exchange resin | 4.0 | 4.0 | 4.0 | 4.0 | 4.0 | 4.0 | 4.0 |
| Elution extraction medium | Amount (g) of 35 wt % hydrochloric acid aqueous solution | 4.0 | 4.0 | 1.0 | 2.0 | 2.0 | 2.0 | 2.0 |
| | Type of non-fluorinated medium | A | A | A | A | A | A | A |
| | Amount (g) of non-fluorinated medium | 4.0 | 4.0 | 4.0 | 1.1 | 2.0 | 5.4 | 2.0 |
| | Type of fluorinated medium | C | C | C | C | C | C | C |
| | Amount (g) of fluorinated medium | 4.0 | 4.0 | 4.0 | 9.8 | 8.0 | 1.3 | 2.0 |
| | Hydrochloric acid/fluorinated medium (mass ratio) | 50/50 | 50/50 | 20/80 | 17/83 | 20/80 | 61/39 | 50/50 |
| | Fluorinated medium/non-fluorinated medium (mass ratio) | 50/50 | 50/50 | 50/50 | 90/10 | 80/20 | 19/81 | 50/50 |
| | Presence or absence of flammability of elution extraction medium | Present | Present | Present | Absent | Present | Present | Present |
| Basic ion exchange resin/elution extraction medium (mass ratio) | | 25/75 | 25/75 | 31/69 | 24/76 | 25/75 | 32/68 | 40/60 |
| Extraction temperature (° C.) | | 40 | 40 | 40 | 40 | 40 | 40 | 40 |
| Extraction time (min) | | 10 | 30 | 30 | 30 | 30 | 30 | 30 |
| Recovery rate (%) of acid of emulsifier | | 94 | 97 | 95 | 87 | 91 | 96 | 95 |

TABLE 1-continued

| NO. | Ex 1-8 | Ex 1-9 | Ex 1-10 | Ex 1-11 | Ex 1-12 | Ex 1-13 | Ex 1-14 |
|---|---|---|---|---|---|---|---|
| Type of basic ion exchange resin | IER-1 | IER-1 | IER-1 | IER-2 | IER-3 | IER-1 | IER-1 |
| Amount (g) of basic ion exchange resin | 4.0 | 4.0 | 4.0 | 3.0 | 4.0 | 4.0 | 4.0 |
| Elution extraction medium — Amount (g) of 35 wt % hydrochloric acid aqueous solution | 2.0 | 2.0 | 2.0 | 3.0 | 2.0 | 2.0 | 2.0 |
| Type of non-fluorinated medium | B | B | B | A | A | — | A |
| Amount (g) of non-fluorinated medium | 4.0 | 2.0 | 4.9 | 3.0 | 4.0 | — | 6.0 |
| Type of fluorinated medium | C | C | C | C | C | C | — |
| Amount (g) of fluorinated medium | 4.0 | 8.0 | 2.1 | 3.0 | 4.0 | 12.0 | — |
| Hydrochloric acid/fluorinated medium (mass ratio) | 33/67 | 20/80 | 49/51 | 50/50 | 33/67 | 14/86 | — |
| Fluorinated medium/non-fluorinated medium (mass ratio) | 50/50 | 80/20 | 30/70 | 50/50 | 50/50 | — | — |
| Presence or absence of flammability of elution extraction medium | Present | Absent | Present | Present | Present | Absent | Present |
| Basic ion exchange resin/elution extraction medium (mass ratio) | 29/71 | 25/75 | 31/69 | 25/75 | 29/71 | 22/78 | 33/67 |
| Extraction temperature (° C.) | 40 | 40 | 40 | 40 | 40 | 40 | 40 |
| Extraction time (min) | 30 | 30 | 30 | 60 | 30 | 30 | 30 |
| Recovery rate (%) of acid of emulsifier | 96 | 97 | 91 | 80 | 96 | 50 | 77 |

IER-1: Manufactured by Lanxess, Lewatit (registered trademark) MonoPlus MP 800 OH, strongly basic ion exchange resin, emulsifier adsorption amount = 28 wt %, porous type
IER-2: Manufactured by Purolite, PUROLITE (registered trademark) A300 MBOH, strongly basic ion exchange resin, emulsifier adsorption amount = 30 wt %, gel type
IER-3: Manufactured by Lanxess, Lewatit (registered trademark) MonoPlus MP 62 WS, weakly basic ion exchange resin, emulsifier adsorption amount = 28 wt %, porous type
Non-fluorinated medium A: acetone
Non-fluorinated medium B: acetonitrile
Fluorinated medium C: 1,3-dichloro-1,1,2,2,3-pentafluoropropane As shown in Table 1, as compared with Ex 1-13 (recovery rate: 50%) wherein extraction was carried out by using hydrochloric acid and a fluorinated medium in combination and Ex 1-14 (recovery rate: 77%) wherein extraction was carried out by using hydrochloric acid and a non-fluorinated medium in combination, in Ex 1-1 to 1-12 wherein extraction was carried out by using an elution extraction medium (a mixture of hydrochloric acid, a non-fluorinated medium and a fluorinated medium), the recovery rate of the acid of the anionic fluorinated emulsifier was high at a level of at least 80% irrespective of the type of the basic ion exchange resin.

Ex 2

In the same manner as in Ex 1, an aqueous solution of an anionic fluorinated emulsifier $(CF_3CF_2OCF_2CF_2OCF_2COO^-(NH_4)^+)$ and a basic ion exchange resin were contacted to let the anionic fluorinated emulsifier be adsorbed on the basic ion exchange resin.

Then, into a beaker having an internal capacity of 50 ml and provided with a cover, the basic ion exchange resin having the anionic fluorinated emulsifier adsorbed thereon and hydrochloric acid were charged as shown in Table 2, and the content was stirred for from 30 to 60 minutes by a magnetic stirrer while maintaining the temperature at from 15 to 60° C. by a constant temperature water bath, whereupon only hydrochloric acid was withdrawn from the beaker.

Then, into the beaker containing the basic ion exchange resin treated with hydrochloric acid, a non-fluorinated medium and a fluorinated medium were charged as shown in Table 2, and the content was stirred for from 30 to 300 minutes by a magnetic stirrer while maintaining the temperature at from 15 to 60° C. by a constant temperature water bath, to carry out extraction of an acid of the anionic fluorinated emulsifier.

After completion of the stirring, the basic ion exchange resin was separated and removed. Then, in each of Ex 2-1 to 2-21, as the liquid phase remaining by separating and removing the basic ion exchange resin was separated into two layers, only the lower layer was recovered.

Thereafter, the acid of the anionic fluorinated emulsifier contained in the recovered liquid phase was quantitatively analyzed by the above-mentioned method, and the recovery rate of the acid of the anionic fluorinated emulsifier was measured. The results are summarized in Table 2.

TABLE 2

| | Ex 2-1 | Ex 2-2 | Ex 2-3 | Ex 2-4 | Ex 2-5 | Ex 2-6 | Ex 2-7 |
|---|---|---|---|---|---|---|---|
| Type of basic ion exchange resin | IER-1 | IER-1 | IER-1 | IER-1 | IER-1 | IER-1 | IER-1 |
| Amount (g) of basic ion exchange resin | 4.0 | 4.0 | 4.0 | 4.0 | 4.0 | 4.0 | 4.0 |
| Concentration (wt %) of hydrochloric acid | 35 | 35 | 35 | 18 | 35 | 18 | 18 |
| Amount (g) of aqueous hydrochloric acid solution | 4.0 | 4.0 | 4.0 | 3.0 | 4.0 | 4.0 | 4.0 |
| Hydrochloric acid treatment temperature (° C.) | 15 | 15 | 40 | 40 | 40 | 40 | 40 |
| Hydrochloric acid treatment time (min) | 30 | 30 | 30 | 30 | 30 | 30 | 30 |
| Basic ion exchange resin/hydrochloric acid (mass ratio) | 50/50 | 50/50 | 50/50 | 57/43 | 50/50 | 50/50 | 50/50 |
| Extraction medium — Type of non-fluorinated medium | A | A | A | B | B | B | B |
| Amount (g) of non-fluorinated medium | 4.0 | 2.0 | 4.0 | 2.0 | 2.0 | 2.0 | 4.0 |
| Type of fluorinated medium | C | C | C | C | C | C | C |
| Amount (g) of fluorinated medium | 4.0 | 2.0 | 4.0 | 8.0 | 8.0 | 8.0 | 4.0 |
| Hydrochloric acid/fluorinated medium (mass ratio) | 50/50 | 67/33 | 50/50 | 27/73 | 33/67 | 33/67 | 50/50 |

TABLE 2-continued

|  |  | | | | | | | |
|---|---|---|---|---|---|---|---|---|
|  | Fluorinated medium/non-fluorinated medium (mass ratio) | 50/50 | 50/50 | 50/50 | 80/20 | 80/20 | 80/20 | 50/50 |
|  | Presence or absence of flammability of extraction medium | Present | Present | Present | Absent | Absent | Absent | Present |
| Basic ion exchange resin/extraction medium (mass ratio) | | 33/67 | 50/50 | 33/67 | 29/71 | 29/71 | 29/71 | 33/67 |
| Extraction temperature (° C.) | | 15 | 15 | 40 | 40 | 40 | 40 | 40 |
| Extraction time (min) | | 30 | 30 | 30 | 30 | 30 | 30 | 30 |
| Extraction rate (%) of acid of emulsifier | | 99 | 88 | 96 | 86 | 88 | 85 | 94 |

|  |  | Ex 2-8 | Ex 2-9 | Ex 2-10 | Ex 2-11 | Ex 2-12 | Ex 2-13 | Ex 2-14 |
|---|---|---|---|---|---|---|---|---|
| Type of basic ion exchange resin | | IER-1 | IER-1 | IER-1 | IER-1 | IER-2 | IER-3 | IER-3 |
| Amount (g) of basic ion exchange resin | | 4.0 | 4.0 | 4.0 | 4.0 | 4.0 | 4.0 | 4.0 |
| Concentration (wt %) of hydrochloric acid | | 18 | 18 | 18 | 18 | 18 | 18 | 18 |
| Amount (g) of aqueous hydrochloric acid solution | | 4.0 | 4.0 | 4.0 | 4.0 | 4.0 | 4.0 | 4.0 |
| Hydrochloric acid treatment temperature (° C.) | | 40 | 40 | 40 | 40 | 60 | 60 | 60 |
| Hydrochloric acid treatment time (min) | | 30 | 30 | 30 | 60 | 30 | 30 | 30 |
| Basic ion exchange resin/hydrochloric acid (mass ratio) | | 50/50 | 50/50 | 50/50 | 50/50 | 50/50 | 50/50 | 50/50 |
| Extraction medium | Type of non-fluorinated medium | B | B | B | B | B | B | B |
|  | Amount (g) of non-fluorinated medium | 2.0 | 1.1 | 5.0 | 2.0 | 6.0 | 6.0 | 3.0 |
|  | Type of fluorinated medium | C | C | C | C | C | C | C |
|  | Amount (g) of fluorinated medium | 8.0 | 4.4 | 2.1 | 4.0 | 6.0 | 6.0 | 12.0 |
|  | Hydrochloric acid/fluorinated medium (mass ratio) | 33/67 | 48/52 | 66/34 | 50/50 | 40/60 | 40/60 | 25/75 |
|  | Fluorinated medium/non-fluorinated medium (mass ratio) | 80/20 | 80/20 | 30/70 | 67/33 | 50/50 | 50/50 | 80/20 |
|  | Presence or absence of flammability of extraction medium | Present | Absent | Present | Present | Present | Present | Absent |
| Basic ion exchange resin/extraction medium (mass ratio) | | 29/71 | 42/58 | 36/64 | 40/60 | 25/75 | 25/75 | 21/79 |
| Extraction temperature (° C.) | | 40 | 40 | 40 | 40 | 60 | 60 | 60 |
| Extraction time (min) | | 60 | 60 | 30 | 60 | 60 | 60 | 90 |
| Extraction rate (%) of acid of emulsifier | | 91 | 85 | 96 | 88 | 83 | 98 | 97 |

|  |  | Ex 2-15 | Ex 2-16 | Ex 2-17 | Ex 2-18 | Ex 2-19 | Ex 2-20 | Ex 2-21 |
|---|---|---|---|---|---|---|---|---|
| Type of basic ion exchange resin | | IER-3 | IER-3 | IER-3 | IER-3 | IER-3 | IER-3 | IER-1 |
| Amount (g) of basic ion exchange resin | | 4.0 | 4.0 | 4.0 | 4.0 | 4.0 | 4.0 | 4.0 |
| Concentration (wt %) of hydrochloric acid | | 18 | 18 | 18 | 18 | 18 | 18 | 18 |
| Amount (g) of aqueous hydrochloric acid solution | | 4.0 | 4.0 | 4.0 | 4.0 | 4.0 | 4.0 | 4.0 |
| Hydrochloric acid treatment temperature (° C.) | | 40 | 40 | 40 | 20 | 20 | 20 | 40 |
| Hydrochloric acid treatment time (min) | | 60 | 60 | 60 | 60 | 60 | 60 | 30 |
| Basic ion exchange resin/hydrochloric acid (mass ratio) | | 50/50 | 50/50 | 50/50 | 50/50 | 50/50 | 50/50 | 50/50 |
| Extraction medium | Type of non-fluorinated medium | B | B | B | B | B | B | — |
|  | Amount (g) of non-fluorinated medium | 4.0 | 4.0 | 4.0 | 4.0 | 3.0 | 2.0 | — |
|  | Type of fluorinated medium | C | C | C | C | C | C | C |
|  | Amount (g) of fluorinated medium | 16.0 | 16.0 | 16.0 | 16.0 | 12.0 | 8.0 | 12 |
|  | Hydrochloric acid/fluorinated medium (mass ratio) | 20/80 | 20/80 | 20/80 | 20/80 | 25/75 | 33/67 | 25/75 |
|  | Fluorinated medium/non-fluorinated medium (mass ratio) | 80/20 | 80/20 | 80/20 | 80/20 | 80/20 | 80/20 | — |
|  | Presence or absence of flammability of extraction medium | Absent | Absent | Absent | Absent | Absent | Absent | Absent |
| Basic ion exchange resin/extraction medium (mass ratio) | | 17/83 | 17/83 | 17/83 | 17/83 | 21/79 | 21/79 | 25/75 |
| Extraction temperature (° C.) | | 50 | 50 | 50 | 50 | 50 | 50 | 40 |
| Extraction time (min) | | 60 | 120 | 300 | 60 | 60 | 60 | 30 |
| Extraction rate (%) of acid of emulsifier | | 95 | 97 | 99 | 95 | 94 | 85 | 44 |

IER-1: Manufactured by Lanxess, Lewatit (registered trademark) MonoPlus MP 800 OH, strongly basic ion exchange resin, emulsifier adsorption amount = 28 wt %, porous type
IER-2: Manufactured by Purolite, PUROLITE (registered trademark) A300 MBOH, strongly basic ion exchange resin, emulsifier adsorption amount = 20 wt %, gel type
IER-3: Manufactured by Lanxess, Lewatit (registered trademark) MonoPlus MP 62 WS, weakly basic ion exchange resin, emulsifier adsorption amount = 26 wt %, porous type
Non-fluorinated medium A: acetone
Non-fluorinated medium B: acetonitrile
Fluorinated medium C: 1,3-dichloro-1,1,2,2,3-pentafluoropropane As shown in Table 2, as compared with Ex 2-21 (recovery rate: 44%) wherein extraction was carried out by using only a fluorinated medium, in Ex 2-1 to 2-20 wherein extraction was carried out by using an extraction medium (a mixture of a non-fluorinated medium and a fluorinated medium), the recovery rate of the acid of the anionic fluorinated emulsifier was high at a level of at least 83%.

INDUSTRIAL APPLICABILITY

According to the method for recovering an anionic fluorinated emulsifier of the present invention, it is possible to recover an anionic fluorinated emulsifier in good yield, the fluorinated medium used for the recovery can be reused, and the time and labor required for waste liquid treatment can be reduced. Further, the recovered anionic fluorinated emulsifier is industrially useful, e.g. since it may be used, as it is or as an alkali metal salt or ammonium salt after neutralization, for e.g. emulsion polymerization of a fluorinated polymer aqueous emulsion.

This application is a continuation of PCT Application No. PCT/JP2012/072802, filed on Sep. 6, 2012, which is based upon and claims the benefit of priority from Japanese Patent Application No. 2011-199724 filed on Sep. 13, 2011. The contents of those applications are incorporated herein by reference in its entirety.

What is claimed is:

1. A method for recovering an anionic fluorinated emulsifier, comprising contacting a mixed liquid comprising an aqueous inorganic acid solution, a fluorinated medium and a non-fluorinated medium to a basic ion exchange resin having an anionic fluorinated emulsifier adsorbed thereon, thereafter separating the basic ion exchange resin and a liquid phase to recover the liquid phase, and recovering, from the liquid phase, the acid of the anionic fluorinated emulsifier.

2. A method for recovering an anionic fluorinated emulsifier, comprising contacting an aqueous inorganic acid solution to a basic ion exchange resin having an anionic fluorinated emulsifier adsorbed thereon, then contacting said basic ion exchange resin with a mixed liquid comprising a fluorinated medium and a non-fluorinated medium, thereafter separating the basic ion exchange resin and a liquid phase to recover the liquid phase, and recovering, from the liquid phase, the acid of the anionic fluorinated emulsifier.

3. The method for recovering an anionic fluorinated emulsifier according to claim 2, wherein after contacting the aqueous inorganic acid solution to the basic ion exchange resin, the basic ion exchange resin is separated and recovered, and to the separated and recovered basic ion exchange resin, the mixed liquid of a fluorinated medium and a non-fluorinated medium, is contacted.

4. The method for recovering an anionic fluorinated emulsifier according to claim 1, wherein the basic ion exchange resin has an average particle size of from 0.1 to 5 mm and an ion exchange capacity of from 0.1 to 3 (eq/L).

5. The method for recovering an anionic fluorinated emulsifier according to claim 2, wherein the basic ion exchange resin has an average particle size of from 0.1 to 5 mm and an ion exchange capacity of from 0.1 to 3 (eq/L).

6. The method for recovering an anionic fluorinated emulsifier according to claim 1, wherein the ratio of the fluorinated medium to the non-fluorinated medium in the mixed liquid is from 5/95 to 95/5 by mass ratio.

7. The method for recovering an anionic fluorinated emulsifier according to claim 2, wherein the ratio of the fluorinated medium to the non-fluorinated medium in the mixed liquid is from 5/95 to 95/5 by mass ratio.

8. The method for recovering an anionic fluorinated emulsifier according to claim 1, wherein the ratio of the basic ion exchange resin to the mixed liquid is from 1/99 to 99/1 by mass ratio.

9. The method for recovering an anionic fluorinated emulsifier according to claim 2, wherein the ratio of the basic ion exchange resin to the mixed liquid is from 1/99 to 80/20 by mass ratio.

10. The method for recovering an anionic fluorinated emulsifier according to claim 1, wherein the aqueous inorganic acid solution is at least one member selected from the group consisting of aqueous solutions of hydrochloric acid, sulfuric acid, nitric acid and phosphoric acid.

11. The method for recovering an anionic fluorinated emulsifier according to claim 2, wherein the aqueous inorganic acid solution is at least one member selected from the group consisting of aqueous solutions of hydrochloric acid, sulfuric acid, nitric acid and phosphoric acid.

12. The method for recovering an anionic fluorinated emulsifier according to claim 1, wherein the fluorinated medium is at least one member selected from the group consisting of 1,3-dichloro-1,1,2,2,3-pentafluoropropane, 1,1-dichloro-2,2,3,3,3-pentafluoropropane, $CF_3CF_2CF_2CF_2CF_2CHF_2$ and $CF_3CH_2OCF_2CF_2H$.

13. The method for recovering an anionic fluorinated emulsifier according to claim 2, wherein the fluorinated medium is at least one member selected from the group consisting of 1,3-dichloro-1,1,2,2,3-pentafluoropropane, 1,1-dichloro-2,2,3,3,3-pentafluoropropane, $CF_3CF_2CF_2CF_2CF_2CHF_2$ and $CF_3CH_2OCF_2CF_2H$.

14. The method for recovering an anionic fluorinated emulsifier according to claim 1, wherein the non-fluorinated medium is water-soluble and has a solubility in the fluorinated medium.

15. The method for recovering an anionic fluorinated emulsifier according to claim 2, wherein the non-fluorinated medium is water-soluble and has a solubility in the fluorinated medium.

16. The method for recovering an anionic fluorinated emulsifier according to claim 1, wherein the non-fluorinated medium is at least one member selected from the group consisting of acetone, acetonitrile, tetrahydrofuran, diethyl ether, methyl acetate, ethyl acetate, methanol, ethanol, n-propanol, iso-propanol and tert-butanol.

17. The method for recovering an anionic fluorinated emulsifier according to claim 2, wherein the non-fluorinated medium is at least one member selected from the group consisting of acetone, acetonitrile, tetrahydrofuran, diethyl ether, methyl acetate, ethyl acetate, methanol, ethanol, n-propanol, iso-propanol and tert-butanol.

18. The method for recovering an anionic fluorinated emulsifier according to claim 1, wherein the mixed liquid is non-flammable.

19. The method for recovering an anionic fluorinated emulsifier according to claim 2, wherein the mixed liquid is non-flammable.

20. The method for recovering an anionic fluorinated emulsifier according to claim 1, wherein the acid of the anionic fluorinated emulsifier is a fluorinated carboxylic acid.

21. The method for recovering an anionic fluorinated emulsifier according to claim 2, wherein the acid of the anionic fluorinated emulsifier is a fluorinated carboxylic acid.

22. The method for recovering an anionic fluorinated emulsifier according to claim 20, wherein the acid of the anionic fluorinated emulsifier is a $C_{5-7}$ fluorinated carboxylic acid which may have from 1 to 3 etheric oxygen atoms.

23. The method for recovering an anionic fluorinated emulsifier according to claim 21, wherein the acid of the anionic fluorinated emulsifier is a $C_{5-7}$ fluorinated carboxylic acid which may have from 1 to 3 etheric oxygen atoms.

24. The method for recovering an anionic fluorinated emulsifier according to claim 1, wherein the basic ion exchange resin is a strongly basic ion exchange resin.

25. The method for recovering an anionic fluorinated emulsifier according to claim 2, wherein the basic ion exchange resin is a strongly basic ion exchange resin.

* * * * *